United States Patent [19]

Hamilton, Jr.

[11] Patent Number: 5,043,520

[45] Date of Patent: Aug. 27, 1991

[54] CONCURRENT ISOMERIZATION AND DISPROPORTIONATION OF OLEFINS

[75] Inventor: David M. Hamilton, Jr., Houston, Tex.

[73] Assignee: Shell Oil Company, Houston, Tex.

[21] Appl. No.: 454,246

[22] Filed: Dec. 21, 1989

[51] Int. Cl.$^5$ .............................................. C07C 6/00
[52] U.S. Cl. .................................. 585/646; 585/666; 585/670
[58] Field of Search .......................... 585/646, 666, 670

[56] References Cited

U.S. PATENT DOCUMENTS

| | | | |
|---|---|---|---|
| 3,261,879 | 7/1966 | Banks | 260/683 |
| 3,340,322 | 5/1967 | Heckelsberg | 260/683 |
| 3,365,513 | 1/1968 | Heckelsberg | 260/683 |
| 3,637,892 | 1/1972 | McGrath et al. | 260/683 D |
| 3,726,938 | 4/1973 | Berger | 260/683 D |
| 3,760,026 | 9/1973 | Reusser et al. | 260/683 D |
| 3,786,112 | 1/1974 | Reusser et al. | 260/683 D |
| 3,792,108 | 2/1974 | Arganbright | 260/683 D |
| 3,872,180 | 3/1975 | Nakatomi et al. | 260/683 D |
| 4,016,245 | 4/1977 | Plank et al. | 423/328 |
| 4,180,524 | 12/1979 | Reusser et al. | 585/644 |
| 4,251,499 | 2/1981 | Nanne et al. | 423/329 |
| 4,335,019 | 6/1982 | Bowes et al. | 502/66 |
| 4,727,203 | 2/1988 | Hamilton | 585/670 |
| 4,749,819 | 6/1988 | Hamilton | 585/666 |

FOREIGN PATENT DOCUMENTS 1128091 3/1966 United Kingdom .
1205677 9/1970 United Kingdom .

*Primary Examiner*—Curtis R. Davis
*Attorney, Agent, or Firm*—Pamela J. McCollough

[57] ABSTRACT

This invention relates to a process for the concurrent isomerization and disproportionation of hydrocarbon olefins by contacting said hydrocarbon at disporportionation conditions with a catalyst comprising a physical mixture of a disproportionation catalyst comprising a heavy metal selected from the group consisting of molybdenum, tungsten, rhenium and mixtures thereof, deposited on an inorganic oxide support and a double bond isomerization catalyst comprising an acidic zeolite capable of effecting double bond isomerization.

21 Claims, No Drawings

CONCURRENT ISOMERIZATION AND DISPROPORTIONATION OF OLEFINS

FIELD OF THE INVENTION

This invention relates to a process for the concurrent disproportionation and isomerization of olefinic hydrocarbons utilizing a physical mixture of a disproportionation catalyst and a double bond isomerization catalyst.

BACKGROUND OF THE INVENTION

Reactions of olefinic molecules in the presence of metal-containing catalysts to produce other olefinic molecules are known in the art as "disproportionation" reactions. The olefin disproportionation reaction can be visualized as the breaking of two existing double bonds between the first and second carbon atoms, and between the third and fourth carbon atoms, respectively, and the formation of two new double bonds, such as between the first and third carbon atoms and the second and fourth carbon atoms, respectively. A typical olefin disproportionation process is illustrated by U.S. Pat. No. 3,261,879, issued July 19, 1966, to Banks, wherein two similar non-symmetrical molecules of an olefin react in the presence of certain catalysts to produce one olefin of a higher carbon number and one olefin of a lower carbon number such as, for example, propylene disproportionation by the process of U.S. Pat. No. 3,261,879 to produce ethylene and butylenes.

As used in this application, disproportionation process means the conversion of olefinic hydrocarbons into similar olefinic hydrocarbons of higher and lower numbers of carbon atoms per molecule. Where the reactant comprises 1- or 2-olefins having relatively long chains, a mixture of products is obtained comprising primarily olefins having both a larger and a smaller number of carbon atoms than the feed olefin but also including other disproportionated products, for example, saturated hydrocarbons, and other converted and unconverted material. Such an operation is useful in many instances. For example, a more plentiful hydrocarbon can be converted to a less plentiful and therefore more valuable hydrocarbon. One instance of such a conversion occurs when the process of this invention is used to convert both higher and lower molecular weight olefins to olefins in the $C_{10}-C_{16}$ range, a range of olefins especially suitable for the manufacture of detergents. Another instance of a disproportionation reaction having considerable value is the disproportionation of propylene to produce ethylene and butene.

A variety of catalysts have been employed for conducting disproportionation reactions, such as those disclosed in U.S. Pat. No. 3,340,322, issued Sept. 5, 1967; U.S. Pat. No. 3,637,892, issued Jan. 25, 1972; U.S. Pat. No. 3,760,026, issued Sept. 18, 1973; U.S. Pat. No. 3,792,108, issued Feb. 12, 1974; U.S. Pat. No. 3,872,180, issued Mar. 18, 1975; and British Patent Specification No. 1,128,091, published Mar. 16, 1966.

It is also known that the presence of a catalyst which possesses double bond isomerization activity in a disproportionation zone is advantageous because it increases the rate of conversion and makes possible the production of a wider range of reaction products. For example, the presence of such double bond isomerization activity greatly increases the disproportionation rate of symmetrical olefins such as butene-2. In addition, the isomerization activity permits the exhaustive cleavage of high molecular weight monoolefins with ethylene to lower molecular weight monoolefins such as propylene and isobutene. British Patent No. 1,205,677, published Sept. 16, 1970, provides a catalyst which comprises an olefin disproportionation component and a Group VIII noble metal double bond isomerization component, i.e., palladium, platinum or ruthenium. Another catalyst system which accomplished the same results is obtained by physically mixing catalytic magnesium oxide with tungsten oxide on silica catalyst. Other catalysts which have been developed include those obtained by copromoting an olefin disproportionation catalyst such as tungsten oxide on silica with minor amounts of the oxides of niobium, tantalum, or vanadium to provide the double bond isomerization activity.

U.S. Pat. No. 3,786,112 discloses a catalyst comprising a physical mixture of an olefin disproportionation catalyst and a double bond isomerization catalyst wherein the double bond isomerization catalyts has been treated with an alkali metal or alkaline metal earth compound.

U.S. Pat. No. 4,180,524 discloses a single catalyst composition containing a support, uranium and at least one of molybdenum, tungsten or rhenium, which provides double bond isomerization activity as well as olefin disproportionation activity.

The catalyst in the above references for isomerization and combined isomerization/disproportionation have either basic or neutral isomerization components. It has been found in the present invention that an acidic isomerization component in combination with a disproportionation component can be used for concurrent isomerization/disproportionation with a low side-product make, thus resulting in a greater quantity of useful olefins.

SUMMARY OF THE INVENTION

The present invention relates to a process for the concurrent isomerization and disproportionation of olefinic hydrocarbons which comprises contacting said olefinic hydrocarbons with a physical mixture of a disproportionation catalyst comprising an element selected from the group consisting of molybdenum, tungsten, rhenium and mixtures thereof, and optionally cobalt, and an isomerization catalyst comprising an acidic zeolite catalyst.

It has been found that the physical mixture catalyst of the present invention results in improved product conversion yield and/or selectivity in a combined olefin isomerization/disproportionation process when compared to a conventionally prepared catalyst useful for disproportionation. The physical mixture catalyst of this invention can be prepared by combining a catalyst comprising a element selected from the group consisting of molybdenum, tungsten, rhenium and mixtures thereof, and optionally cobalt, on an inorganic oxide support with an acidic zeolite catalyst. In an olefin production process combining the steps of oligomerization, isomerization and disproportionation such as that disclosed in U.S. Pat. No. 3,726,938, issued to Berger, it is preferred to use catalysts prepared according to the instant invention in the disproportionation zone.

DESCRIPTION OF THE PREFERRED EMBODIMENTS

In the process of the instant invention, the concurrent isomerization and disproportionation of an olefinic hydrocarbon is accomplished by contacting the olefinic hydrocarbon with a physical mixture of a disproportionation catalyst comprising an element selected from the group consisting of molybdenum, tungsten, rhenium and mixtures thereof, and optionally cobalt, on an inorganic oxide support and a double bond isomerization catalyst comprising an acidic zeolite.

As used herein, "zeolite" refers to a crystalline aluminosilicate with a framework based on an extensive three-dimensional network of oxygen ions. Situated within the tetrahedral sites formed by the oxygen can be either a Si(+4) or an Al(+3) ion. The AlO$_2$(−) tetrahedra in the structure determine the framework charge. A representative empirical formula for a zeolite is written as:

$$M_{(2/n)} \cdot Al_2O_3 \cdot xSiO_2 \cdot yH_2O,$$

where M represents the exchangeable cations, generally from the group I or II ions, although other metal, non-metal and organic cations may also be used to balance the framework charge and n represents the cation charge. These cations are present either during synthesis, through post-synthesis ion exchange. The value of x is equal to or greater than 2 because Al (+3) does not occupy adjacent tetrahedral sites. The crystalline framework structure contains voids and channels of discrete size with pore or channel openings ranging from 3 Å to 8 Å, depending on the structure. Typical cations include: the alkali and alkaline earth cations, ammonium, tetramethylammonium and other nitrogen-containing organic cations, and the rare earth and nobel metal ions. As used herein, "acidic zeolite" refers to those zeolites where the charge balancing cation is a proton, H(+).

Olefins which are subjected to concurrent isomerization and disproportionation according to the process of this invention include $C_3{}^+$ olefinic hydrocarbons or $C_3{}^+$ internal olefins in combination with ethylene. A useful group of feed materials are olefinic hydrocarbons having carbon numbers ranging from $C_2$ to about $C_{100}$ and mixtures thereof, preferably from $C_2$ to about $C_{60}$ and mixtures thereof, and more preferably linear olefinic hydrocarbons having carbon numbers ranging from about $C_4$ to about $C_{40}$ and mixtures thereof. Examples of compounds most suitable for disproportionation according to this invention are acyclic 1- and 2-alkenes, and alkyl and aryl derivatives thereof having from 3 to 20 carbon atoms per molecule. Some specific examples of such olefins are propylene, 1-butene, 2-butene, 1-pentene, 2-pentene, 1-hexene, 2-heptene, 1-octene, 2-nonene, 1-dodecene, 2-tetradecene, 1-hexadecene, 2-methyl-1-butene, 2-methyl-2-butene, 3-methyl-1-butene, 1-phenylbutene-2, and 3-heptene. Higher disproportionation conversions and wider product distributions are obtained at comparable reaction times with 1-olefins than with 2-olefins. 3-olefins are disproportionated at still lower rates.

The feed should be essentially free of impurities which adversely affect the reaction. A subsequent reactivation of the catalyst to remove the effect of such impurities can be made repeatedly by heat treatment with air, using an inert gas to control burn-off temperature.

The physical mixture catalyst of this invention is prepared by combining a supported disproportionation catalyst containing an element selected from the group consisting of molybdenum, tungsten, rhenium and mixtures thereof, and optionally cobalt, and a double bond isomerization catalyst comprising an acidic zeolite.

The disproportionation catalyst comprises molybdenum and/or tungsten and/or rhenium supported on an alumina-containing support. In a preferred embodiment, the catalyst also contains cobalt. Any conventional catalytic grade of alumina including the beta or gamma forms can be used. The catalyst can contain other materials which do not substantially promote undesirable side reactions. For example, an alumina support or base can contain silica, magnesia, titania or other bases in amounts which do not change the essential characteristics of the reaction.

The disproportionation catalyst can be prepared by any conventional method such as dry mixing, coprecipitation or impregnation. For example, a 10–100 mesh alumina can be impregnated with an aqueous solution containing molybdenum salts, such as ammonium dimolybdate and optionally, cobalt salts, such as cobalt nitrate.

In a preferred embodiment, the disproportionation catalyst in the instant invention is a cobalt/molybdenum catalyst prepared by impregnating alumina with an impregnation solution combining an aqueous cobalt solution and an aqueous molybdenum solution. The cobalt solution consists of cobalt salts dissolved in water. A wide range of cobalt compounds are suitable, such as cobalt nitrate, cobalt hydroxide, cobalt acetate, cobalt oxalate, or cobalt oxide, with cobalt nitrate being preferred. The molybdenum solution consists of a water-soluble source of molybdenum oxide such as ammonium heptamolybdate or ammonium dimolybdate dissolved in water. Hydrogen peroxide may also be used to aid in solution preparation in some cases. A preferred method for preparing the molybdenum solution consists of adding hydrogen peroxide to the solution in the range of about 0.1 to about 1.0 mole of hydrogen peroxide per mole of molybdenum. Optionally, a suitable soluble amine compound such as monoethanolamine, propanolamine or ethylenediamine may be added to the molybdenum solution in order to aid in stabilization of the solution.

Following impregnation, the resulting material is dried and calcined. Drying is accomplished by conventional means. It may be carried out by forced draft drying, vacuum drying, air drying or similar means. Drying temperatures are not critical and depend upon the particular means utilized for drying. Drying temperatures will typically range from about 50° C. to about 150° C.

After drying, the material is calcined to produce the finished catalyst. The material may be calcined in an oxidizing or neutral atmosphere, although air is preferred. However, if binders and/or lubricants are used the material is heated in an oxygen-containing atmosphere, preferably air, in order to burn out the binders and lubricants. Calcining temperatures will typically range from about 300° C. to about 600° C. Burn-out temperatures will depend on the concentration of oxygen in the burn-out atmosphere as well as the burn-out time involved. Typically, burn-out temperatures will range from about 300° C. to about 600° C. Drying, calcining and burn-out may be combined in one or two steps. Most frequently the calcining and/or burn-out steps are combined using an oxygen-containing atmosphere.

The final catalysts typically contain from about 5 percent by weight to about 18 percent by weight molybdenum, about 8 percent by weight to about 32 percent by weight tungsten or from about 1 percent by weight to about 20 percent by weight rhenium. When mixtures of molybdenum, and tungsten and rhenium are utilized, the final catalyst typically contains from about 5 percent by weight to about 32 percent by weight molybdenum and/or tungsten and/or rhenium. When the catalyst contains cobalt, the final catalyst contains from about 0.1 percent by weight to about 5 percent by weight cobalt. These types of catalysts are well known in the prior art and reference can be prepared according to the prior art, such as but not limited to aforementioned U.S. Pat. No. 3,261,879 and U.S. Pat. No. 3,365,513 (both of which are incorporated by reference herein) for more specific details about these types of catalysts.

The double bond isomerization catalysts which are suitable for use in the instant invention are acidic zeolites. Suitable acidic zeolite include ferrierite, ZSM-35, ZSM-5, mordenite, fujasite, and the like. In a preferred embodiment, the acidic zeolite catalyst is ferrierite. Ferrierite is a naturally occuring zeolite mineral having a composition which varies somewhat with the particular source.

The prominent structural features of ferrierite have been found by X-ray crystal determination to be parallel channels in the aluminosilicate framework. The ferrierite is a two dimensional zeolite consisting of intersecting 8 and 10 ring channels. The larger 4.3 Å×5.5 Å ten ring channel parallels the c crystallographic axis, while the smaller 3.4 Å×4.8 Å eight ring channel parallels the b crystallographic axis. Practically speaking, the larger ten ring channel is the only diffusion path available to a molecule of any moderate size. Therefore, the channel system of ferrierite is essentially undimensional due to practical considerations.

Suitable ferrierite catalysts are exemplified by the ZSM-35 aluminosilicate of U.S. Pat. No. 4,016,245 or most preferably by a piperidine derived ferrierite as discussed in U.S. Pat. No. 4,251,499, all of the teachings of which are incorporated by reference herein. Ferrierite aluminosilicate catalysts are typically prepared by in the manner described in U.S. Pat. No. 4,251,499, in which an aqueous mixture having one or more compounds of an alkali metal, one or more aluminum compounds, one or more silicon compounds and at least one compound selected from piperidine and alkyl- substituted piperidine is formed and maintained at a temperature of 100° C. to 200° C. until the ferrierite has formed, followed by recovery of the ferrierite crystals.

In one embodiment, the ferrierite catalyst is treated with methylsilylating agents or organofunctional silylating or silane agents in order to reduce undesirable dimerization reactions which often accompany olefin isomerization. These agents are believed to be responsible for modifying the catalyst sites on the ferrierite aluminosilicate surface and thereby reducing access to dimerization sites for the olefin feed material. A list of suitable silyating agents is set forth in Kirk-Othmer, vol. 18 at pages 260–268, the teachings of which are hereby incorporated by reference. A non-limiting list of suitable silylating agents includes 1,1,1,3,3,3, -hexamethyldisilazane, trimethylchlorosilane, n-trimethylsilylacetamide, tetramethyldisilazane, bis(trimethylsilyl)acetamide, vinyltriacetoxysilane, dimethylchlorosilane, bromomethyldimethylchlorosilane, di(chloromethyl)-tetramethyldisilazane, vinyltriethoxysilane and the like, with 1,1,1,3,3,3-hexamethyldisilazane being preferred.

The catalyst of the instant invention is prepared by admixing the disproportionation catalyst and the double bond isomerization catalyst. To facilitate mixing, it is desirable to have the catalysts in a form which is compatible one with the other. The catalysts may be, for example, in the form of powders, extrudates, pills and the like prior to mixing the two catalysts together. The amount of disproportionation catalyst used in the physical catalyst mixture is generally in excess of the amount of double bond isomerization catalyst used in the mixture. Preferably the ratio of disproportionation catalyst to double bond isomerization catalyst in the physical mixture is from about 50:1 to about 0.02:1, preferably from about 25:1 to about 0.5:1, and more preferably, from about 10:1 to about 1:1. Particularly preferred is a 9:1 ratio of disproportionation catalyst to double bond isomerization catalyst in the physical mixture.

The physical mixture catalyst system must be activated prior to use in the combined isomerization/disproportionation process. Although each of the individual catalysts can be activated prior to mixing the two catalysts together, it is preferred that the catalyst system be activated after the disproportionation catalyst and isomerization catalyst have been admixed and placed in a suitable reactor. While activation is usually accomplished by contacting the physical mixture catalyst system with an oxygen-containing gas at elevated temperatures, other activation methods such as heating under a vacuum, or contact with various gases such as nitrogen or argon at high temperatures, can be used. The temperature, contact times, and other conditions of activation have been reported in the prior art and are generally the same conditions which are utilized to activate a disproportionation catalyst. Typically, the activation conditions include a temperature in the range of from about 300° C. to about 900° C. for about 30 minutes to about 24 hours.

The combined isomerization/disproportionation process of the invention can be carried out either batchwise or continuously, using a fixed catalyst bed, or a stirrer equipped reactor or other mobile catalyst contacting process as well as any other well known contacting technique. Preferred reaction conditions, e.g., temperature, pressure, flow rates, etc., vary somewhat depending upon the specific catalyst composition, the particular feed olefin, desired products, etc. The process is carried out at temperatures ranging from about 10° C. to about 350° C. and at pressures in the range of about 50 psig to about 500 psig. The isomerization/ disproportionation reaction is usually effected in a liquid phase in the presence of a small amount of ethylene and if desired, liquid reaction diluents are utilized. Examples of suitable diluents are hydrocarbons free from aliphatic unsaturation, such as acyclic or alicyclic alkanes of from 6 to 12 carbon atoms, i.e. hexane, isooctane and cyclohexane. Also exemplary would be monoaromatic compounds such as benzene and toluene. If the diluent is added, it is present in amounts up to 20 moles of diluent per mole of olefinic reactants.

The operable range of contact time for the process of this invention depends primarily upon the operating temperature and the activity of the catalyst, which is influenced by surface area, promoter concentration, activation temperature, etc. In general, the distribution of products is not drastically altered by variation in contact time. Shorter contact times are usually associated with higher temperatures, but, when larger amounts of higher molecular weight products are desired, a suitable combination of contact time and temperature is selected. With proper selection of conditions and contact times, very high efficiency of conversion to desired products can be obtained.

In this application, space rates are given in WHSV (weight hourly space velocity; weight of reactant feed per weight of catalyst per hour).

With a fixed bed reactor, continuous flow operation at pressures in the range of about 50 psig to about 500 psig, preferably about 150 psig to about 250 psig, with catalysts having densities ranging from about 0.5 gram per cc to about 1.0 gram per cc and surface areas greater than about 300 $m^2/g$, and at temperatures in the range of about 10° C. to about 350° C., preferably about 100° C. to about 250° C., weight hourly space velocities in the range of about 0.1 to about 10.0 parts by weight of olefinic hydrocarbon feed per part by weight of catalyst per hour are suitable. The space velocity is adjusted according to changes in density of feed due to change of pressure or temperature, and variation in reaction temperature and the activity of the catalyst. The higher space velocities in general are associated with higher reaction temperatures.

The physical mixture catalyst system of the present invention is advantageous with respect to a catalyst system in which the olefin feed is only disproportionated rather than isomerized and disproportionated concurrently in that a different mixture of product olefins is obtained. The ability to shift the mixture of product olefins is particularly useful in maximizing the economic return from any given olefin feedstock.

The ranges and limitations provided in the instant specification and claims are those which are believed to particularly point out and distinctly claim the instant invention. It is, however, understood that other ranges and limitations that perform substantially the same function in substantially the same manner to obtain the same result are intended to be within the scope of the instant invention as defined by the instant specification and claims.

The process of the instant invention will be further described below by the following examples which are illustrative and which are not to be construed as limiting the invention.

ILLUSTRATIVE EMBODIMENTS

Catalyst Preparation

Catalyst A

Catalyst A is a physical mixture of a cobalt/molybdenum disproportionation catalyst and a ferrierite aluminosilicate double bond isomerization catalyst.

The disproportionation catalyst was prepared using a conventional dry pore volume impregnation technique. A solution suitable for impregnating 75 grams of calcined alumina support with a pore volume of 0.69 $cm^3/g$ was prepared as follows. An impregnation solution was made by combining 5.78 grams of cobalt nitrate, 12.86 grams of ammonium dimolybdate and enough 24% aqueous ammonia to bring the solution to a total volume of 51 milliliters. After adding the entire solution to the alumina support in several small portions with intermediate agitations, the impregnated support was dried overnight at 150° C. and calcined in air for 2 hours at 450° C.

The double bond isomerization catalyst was prepared by incorporation of the organic base, piperidine, with stirring into a solution of sodium water glass (28% $SiO_2$, 8% $Na_2O$) in water. To the mixture thus obtained was added a solution of aluminum sulfate in water or a mixture of water and sulfuric acid with stirring. The targeted molar composition for the starting mixture was 93.5 $SiO_2$; 4 $Al_2O_3$; 10 $Na_2O$; 17 $Na_2SO_4$; 36.7 piperidine; and 1938 $H_2O$. The resultant mixture was stirred for another 15 minutes and then maintained at a temperature of 150° C. for at least 25 hours. The solid product was isolated from the reaction mixture. The resultant solid product was exchanged twice with an aqueous 2M solution of $NH_4NO_3$ to yield ammonium ferrierite. The ammonium ferrierite wa converted to hydrogen ferrierite by calcination in air for two hours at a temperature of at least 300° C.

The two catalysts were then mixed by adding nine parts of the disproportionation catalyst to one part of the double bond isomerization catalyst, followed by agitation to produce a uniform mixture of the two catalysts. The properties of the catalyst are listed in Table I.

Catalyst B

Catalyst B was prepared in a manner similar to Catalyst A except that the ferrierite aluminosilicate catalyst was silylated prior to admixing with the cobalt/molybdenum catalyst utilizing the following silylation procedure. A total of 12.1 grams of ammonium ferrierite as 16-45 mesh powder was refluxed in hexane along with 8 grams of 1,1,1,3,3,3,-hexamethyldisilazane for 1 to 2 hours. The silylated ferrierite was then washed with hexane and dried under $N_2$ at 120° C. for 16 hours. The properties of the catalyst are listed in Table I.

Catalyst C

Catalyst C is a conventional disproportionation catalyst prepared using a conventional dry pore volume impregnation technique. A solution suitable for impregnating 75 grams of calcined alumina support with a pore volume of 0.69 $cm^3/g$ was prepared as follows. An impregnation solution was made by combining 5.78 grams of cobalt nitrate, 12.86 grams of ammonium dimolybdate and enough 24% aqueous ammonia to bring the solution to a total volume of 51 milliliters. After adding the entire solution to the alumina support in several small portions with intermediate agitations, the impregnated support was dried overnight at 150° C. and calcined in air for 2 hours at 450° C. The properties of the catalyst are listed in Table I.

Catalyst Testing

Catalysts A, B, and C were each tested utilizing the following procedure. Twenty $cm^3$ of 16-45 mesh catalyst particles diluted 1/1 with 80 mesh SiC are charged to a stainless steel reactor to obtain a bed length of 8 inches. The catalyst is heated at a temperature of 550° C. under flowing nitrogen for 12 hours to remove any residual water from the catalyst. The catalyst is then cooled to 25O° F. and feed is introduced at a weight hourly space velocity (WHSV) of about 1.5. The feed for these reactions is an equilibrium mixture of decenes prepared by the isomerization of 1-decene. The feed contains approximately 1.5% branched decenes. The results of catalyst testing are presented in Table II.

As mentioned previously, the physical mixture catalysts prepared by the process of the instant invention have improved conversion rates and a wider range of reaction products than conventional disproportionation catalysts in a disproportionation reaction zone. The data in Table II shows the carbon number distributions for Catalysts A, B and C. It is evident from these data that Catalyst A yields a comparable amount of $C_3$-$C_8$ olefin product, less $C_9$-$C_{14}$ olefin product and more $C_{15}$-$C_{28}$ olefin product then the standard, Catalyst C. Catalyst B yields a comparable amount of $C_3$-$C_5$ olefin product, less $C_6$-$C_{12}$ olefin product and more $C_{13}$-$C_{28}$ olefin product than the standard, Catalyst C. The general effect of both Catalyst A and B is to shift the overall olefin product distribution to favor heavier olefins versus the product obtained with the standard, Catalyst C. Catalyst A yields a slightly lighter olefin product as compared with Catalyst B because of differences in the pretreatment of the isomerization catalyst function, specifically, silylation.

TABLE I

| Catalyst | Catalyst Properties | | |
|---|---|---|---|
|  | A | B | C |
| Ratio Disp. Catalyst/ Isom. Catalyst | 9:1 | 9:1 | — |
| Grams Disp. Catalyst | 12.1 | 12.0 | 13.4 |
| Grams Isom. Catalyst | 0.9 | 1.1 | — |
| Disp. Catalyst Composition |  |  |  |
| % wt Mo[a] | 8.1 | 8.1 | 8.1 |
| % wt Co[b] | 3.2 | 3.2 | 3.2 |
| Isom. Catalyst Composition | H$^+$ Ferrierite | Si—H$^+$ Ferrierite | — |

[a] Weight percent determined by neutron activation analysis or atomic absorption spectroscopy.
[b] Weight percent determined by neutron activation analysis or atomic absorption spectroscopy.

TABLE II

| Catalyst | A | B | C |
|---|---|---|---|
| Catalyst Properties | | | |
| $C_{10}$ Feed | Iso. $C_{10}$ | Iso. $C_{10}$ | Iso. $C_{10}$ |
| Reaction Temperature, °F. | 250 | 250 | 250 |
| Catalyst Hours | 3 | 2.75 | 3 |
| Catalyst Volume, cm$^3$ | 20 | 20 | 20 |
| Catalyst Weight, gm | 13.4 | 13.4 | 13.4 |
| WHSV | 1.8 | 1.4 | 1.5 |
| Carbon Number Distribution | | | |
| $C_2$ | 0.000 | 0.000 | 0.000 |
| $C_3$ | 0.045 | 0.032 | 0.027 |
| $C_4$ | 1.126 | 0.075 | 0.743 |
| $C_5$ | 2.214 | 1.387 | 1.646 |
| $C_6$ | 4.189 | 2.626 | 3.574 |
| $C_7$ | 5.925 | 3.787 | 5.693 |
| $C_8$ | 7.584 | 5.227 | 8.166 |
| $C_9$ | 9.086 | 7.195 | 10.542 |
| $C_{10}$ | 11.356 | 9.555 | 13.817 |
| $C_{11}$ | 10.283 | 10.443 | 13.053 |
| $C_{12}$ | 9.768 | 10.921 | 12.281 |
| $C_{13}$ | 8.700 | 10.621 | 10.345 |
| $C_{14}$ | 7.437 | 9.786 | 8.091 |
| $C_{15}$ | 5.970 | 8.198 | 5.462 |
| $C_{16}$ | 4.540 | 6.325 | 3.290 |
| $C_{17}$ | 3.346 | 4.766 | 1.454 |
| $C_{18}$ | 2.514 | 3.456 | 0.721 |
| $C_{19}$ | 2.116 | 2.222 | 0.414 |
| $C_{20}$ | 1.205 | 1.154 | 0.245 |
| $C_{21}$ | 0.819 | 0.670 | 0.243 |
| $C_{22}$ | 0.559 | 0.418 | 0.057 |
| $C_{23}$ | 0.371 | 0.256 | 0.063 |
| $C_{24}$ | 0.238 | 0.151 | 0.026 |
| $C_{25}$ | 0.175 | 0.115 | 0.018 |
| $C_{26}$ | 0.276 | 0.215 | 0.012 |
| $C_{27}$ | 0.157 | 0.113 | 0.011 |
| $C_{28}$ | 0.000 | 0.000 | 0.007 |

I claim as my invention:

1. A process for the concurrent disproportionation and isomerization of olefinic hydrocarbons having carbon numbers ranging from $C_2$ to about $C_{100}$ which comprises contacting said olefinic hydrocarbons with a catalyst comprising a physical mixture of a disproportionation catalyst comprising a heavy metal selected from the group consisting of molybdenum, tungsten, rhenium and mixtures thereof, deposited on an inorganic oxide support and a double bond isomerization catalyst comprising an acidic zeolite capable of effecting double bond isomerization.

2. The process of claim 1 wherein said disproportionation catalyst additionally contains cobalt.

3. The process of claims 1 or 2 wherein a ratio of disproportionation catalyst to double bond isomerization catalyst in the range of from about 50:1 to about 0.02:1 is used.

4. The process of claims 1 or 2 wherein a ratio of disproportionation catalyst to double bond isomerization catalyst in the range of from about 25:1 to about 0.5:1 is used.

5. The process of claim 1 wherein said disproportionation catalyst contains from about 8 percent by weight to about 32 percent by weight heavy metal.

6. The process of claim 5 wherein said disproportionation catalyst contains from about 8 percent by weight to about 18 percent by weight molybdenum.

7. The process of claim 2 wherein said disproportionation catalyst contains from about 1 percent by weight to about 5 percent by weight cobalt and from 8 percent by weight to about 32 percent by weight heavy metal.

8. The process of claim 2 wherein said disproportionation catalyst contains from about 2.5 percent by weight to about 4 percent by weight cobalt and from about 8 percent by weight to about 18 percent by weight molybdenum.

9. The process of claim 1 wherein said olefinic hydrocarbons have carbon numbers ranging from $C_2$ to about $C_{60}$.

10. The process of claim 1 wherein said process is carried out at a temperature in the range of from about 10° C. to about 350° C. and a pressure in the range of from about 50 psig to about 500 psig.

11. A process for the concurrent isomerization and disproportionation of olefinic hydrocarbons having carbon numbers ranging from $C_2$ to about $C_{100}$ which comprises contacting said olefinic hydrocarbons with a catalyst comprising a physical mixture of a disproportionation catalyst comprising a heavy metal selected from the group consisting of molybdenum, tungsten, rhenium and mixtures thereof, deposited on an inorganic oxide support and a double bond isomerization catalyst comprising ferrierite.

12. The process of claim 11 wherein said disproportionation catalyst additionally contains cobalt.

13. The process of claims 11 or 12 wherein a ratio of disproportionation catalyst to double bond isomerization catalyst in the range of from about 50:1 to about 0.02:1 is used.

14. The process of claims 11 or 12 wherein a ratio of disproportionation catalyst to double bond isomerization catalyst in the range of from about 25:1 to about 0.5:1 is used.

15. The process of claim 11 wherein said disproportionation catalyst contains from about 8 percent by weight to about 32 percent by weight heavy metal.

16. The process of claim 15 wherein said disproportionation catalyst contains from about 8 percent by weight to about 18 percent by weight molybdenum.

17. The process of claim 12 wherein said disproportionation catalyst contains from about 1 percent by weight to about 5 percent by weight cobalt and from 8 percent by weight to about 32 percent by weight heavy metal.

18. The process of claim 12 wherein said disproportionation catalyst contains from about 2.5 percent by weight to about 4 percent by weight cobalt and from about 8 percent by weight to about 18 percent by weight molybdenum.

19. The process of claim 11 wherein said olefinic hydrocarbons have carbon numbers ranging from $C_2$ to about $C_{60}$.

20. The process of claim 11 wherein said process is carried out at a temperature in the range of from about 10° C. to about 350° C. and a pressure in the range of from about 50 psig to about 500 psig.

21. A process for the concurrent isomerization and disproportionation of olefinic hydrocarbons having carbon numbers ranging from $C_2$ to about $C_{100}$ which comprises contacting said olefinic hydrocarbons at a temperature in the range of from about 10° C. to about 350° C. and a pressure in the range of from about 50 psig to about 500 psig with a catalyst comprising a physical mixture of a disproportionation catalyst comprising cobalt and a heavy metal selected from the group consisting of molybdenum, tungsten, rhenium and mixtures thereof, deposited on an inorganic oxide support and a double bond isomerization catalyst comprising ferrierite, wherein a ratio of disproportionation catalyst to double bond isomerization catalyst in the range of from about 25:1 to about 0.5:1 is used.

* * * * *